United States Patent [19]
Hess

[11] Patent Number: 5,197,978
[45] Date of Patent: Mar. 30, 1993

[54] REMOVABLE HEAT-RECOVERABLE TISSUE SUPPORTING DEVICE

[75] Inventor: Robert L. Hess, Portola Valley, Calif.

[73] Assignee: Advanced Coronary Technology, Inc., Menlo Park, Calif.

[21] Appl. No.: 691,823

[22] Filed: Apr. 26, 1991

[51] Int. Cl.⁵ .................. A61F 2/06; A61M 29/00
[52] U.S. Cl. ........................... 623/1; 623/11; 623/12; 606/194
[58] Field of Search ............... 606/191–198; 604/96; 428/913; 623/1, 11, 12

[56] References Cited

U.S. PATENT DOCUMENTS

| | | | |
|---|---|---|---|
| 4,390,599 | 6/1983 | Broyles | 428/597 |
| 4,485,816 | 12/1984 | Krumme | 128/334 |
| 4,503,569 | 3/1985 | Dotter | 606/191 |
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 4,893,623 | 1/1990 | Rosenbluth | 606/192 |
| 4,969,458 | 11/1990 | Wiktor | 606/194 |
| 4,969,890 | 11/1990 | Sugita et al. | 606/192 |
| 4,984,581 | 1/1991 | Stice | 128/772 |
| 4,998,539 | 3/1991 | Delsanti | 606/194 |
| 5,002,563 | 3/1991 | Pyka et al. | 606/222 |
| 5,037,427 | 8/1991 | Harada et al. | 606/194 |
| 5,071,407 | 12/1991 | Termin et al. | 606/194 |
| 5,089,005 | 2/1992 | Harada | 606/194 |

*Primary Examiner*—David J. Isabella
*Assistant Examiner*—Debra S. Brittingham
*Attorney, Agent, or Firm*—Burns, Doane, Swecker & Mathis

[57] ABSTRACT

A tissue supporting device, preferably a stent-like member of shape-memory alloy, that is expandable by angioplasty apparatus or the like is subsequently removable by heat recovery to its original, non-expanded configuration.

20 Claims, 4 Drawing Sheets

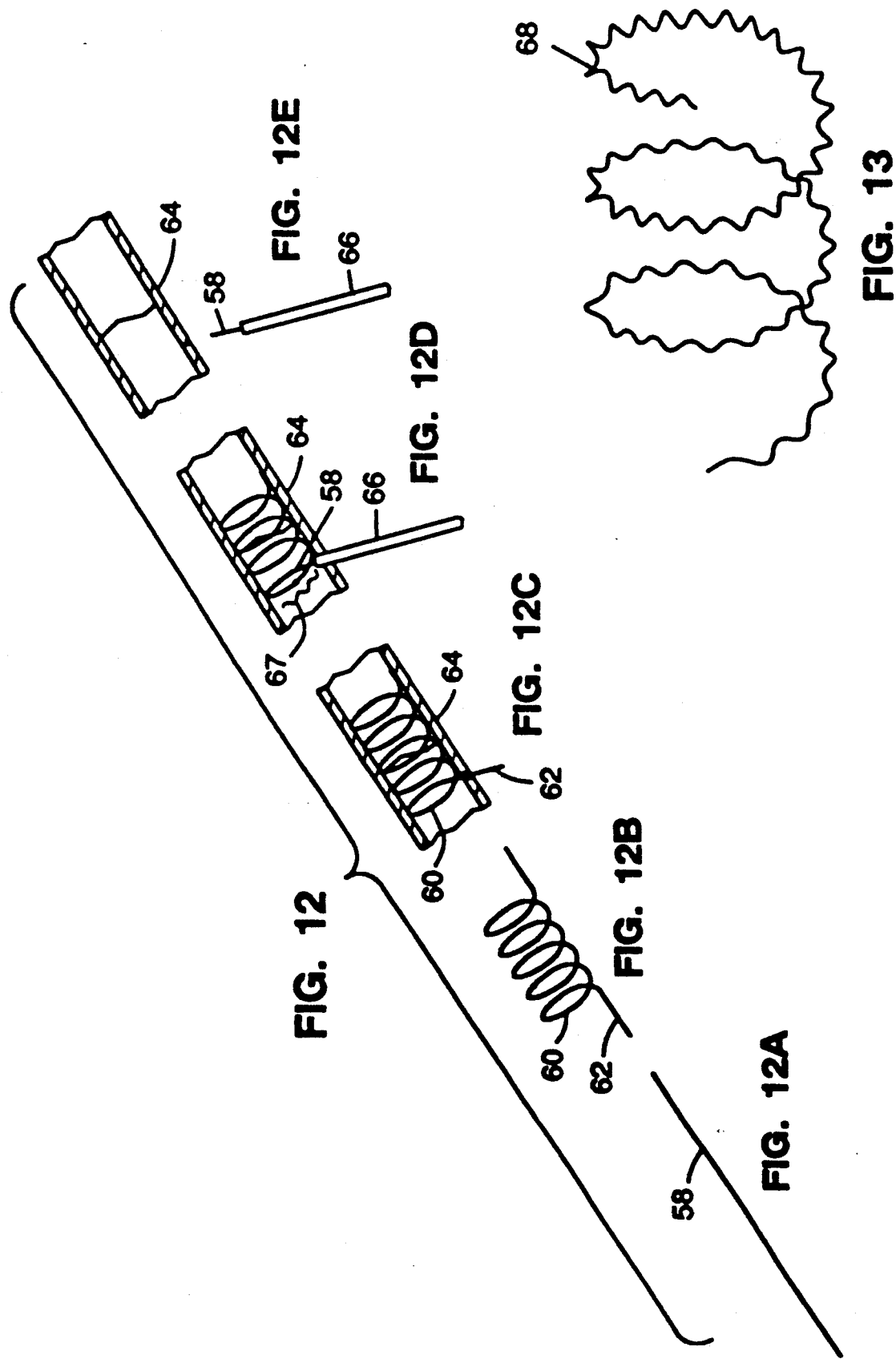

REMOVABLE HEAT-RECOVERABLE TISSUE SUPPORTING DEVICE

BACKGROUND OF THE INVENTION

1. Field of the Invention

This invention relates to tissue supporting devices, preferably vascular stents for repairing blood vessels and, more particularly, to removable devices which will temporarily and, if desired, permanently support a dilated stenosis of a tubular organ (hollow viscus) such as a blood vessel.

2. Description of the Prior Art

In the past, permanent or biodegradable devices have been developed for implantation within a body passageway to maintain vascular patency. These devices are typically characterized by the ability of such an intravascular device to be enlarged radially after having been introduced percutaneously, to be transported transluminally, and to be positioned in a desired location. These devices are either expanded mechanically, such as by the expansion of a mandrel positioned inside the device, or are capable of releasing stored energy to expand themselves upon actuation within the body.

Biodegradable stent-like members using suture materials in braided tubing or the like have been used as vascular stents. Unfortunately, such devices are limited in strength and application and require a relatively long period of time to dissolve.

U.S. Pat. Nos. 4,739,762, 4,776,337 and 4,733,665 disclose expandable and deformable intraluminal vascular grafts in the form of thin-walled tubular members which are expanded radially outwardly into contact with a body passageway, the members being plastically deformed beyond their elastic limit and the members being permanently fixed within the body. Suitable materials for the fabrication of these tubular-shaped members would include silver, tantalum, stainless steel, gold, titanium, or other suitable plastic materials which may be permanently deformed. Permanent deformation is achieved when the material is subjected to a force which is greater than the elastic limit of the material which is utilized to make the tubular member. The open-mesh configuration of such devices is soon encapsulated by body tissue and cannot be removed. The exceeding of the elastic limit of the material used in such devices is also believed to compromise the performance of the devices in situ.

U.S Pat. No. 4,969,458 discloses a vascular stent formed from a wire component made of material, such as copper alloy, titanium, or gold, wherein the wound configuration unwinds upon expansion and becomes a permanent prosthesis stent, similar to prior art devices disclosed above, and is, unfortunately, not removable.

U.S. Pat. No. 4,969,890 discloses various configurations of shape-memory alloy members which have been previously radially compressed and which, upon positioning within the body and thermal activation, expand by themselves to become a permanent prosthesis within the body. In this regard, the reference teaches a device which operates in a similar fashion to the device disclosed in U.S. Pat. No. 4,485,816. U.S. Pat. No. 4,485,816 discloses a shape-memory alloy staple which, when heated, penetrates and cinches tissue together. Shape-memory alloy historically has been used to perform work in such a fashion wherein the component remains in a strong austenitic state after temperature activation. That is, above its transition temperature from martensite to austenite, and as the references above disclose, the shape-memory alloy either dilates an incompetent blood vessel or holds segments of tissue together. Unfortunately, neither of these devices is practically removable.

It would therefore be advantageous to have a tissue supporting device that could be inserted into the body while in a dimensionally compact configuration and deformed mechanically and elastically into position while remaining in that deformed configuration to perform a function such as radial support, engagement with a thrombus, etc., the device remaining somewhat flexible to accommodate movement of soft tissue, the device further being subsequently removable. The subject invention provides such a device using shape-memory alloy in ways different, essentially the opposite, from those taught in the prior art.

SUMMARY OF THE INVENTION

The purpose of the invention is to provide tissue supporting devices that are readily insertable in a first configuration and then elastically deformable into a second configuration wherein the device exhibits a high degree of flexibility, the device being subsequently readily removable at will. To accomplish this purpose, there is provided a heat-recoverable tissue supporting device of nickel-titanium shape-memory alloy having a martensitic state, an austenitic state, and a transition temperature therebetween wherein the device is elastically deformable from a first configuration to a second configuration while in its martensitic state, the device being recoverable to the first configuration upon heating of the device above the transition temperature to the austenitic state for subsequent removal of the device. By way of illustration but not limitation, a tissue supporting device includes members which support, filter, clamp, staple or the like which hold tissue together or separate tissue, etc.

In one aspect of the invention there is provided a tissue supporting device comprising a recoverable member of generally tubular shape of nickel-titanium shape-memory alloy, said alloy having martensitic and austenitic metallurgical states and a transition temperature therebetween, said recoverable member being insertable within a patient while in said martensitic state and being elastically deformable from a first configuration while in said martensitic state to a second configuration, said recoverable member providing tissue support while in said second configuration and being recoverable to said first configuration upon heating of said recoverable member above said transition temperature to said austenitic state for removal of said recoverable member from a patient.

In yet another aspect of the invention there is provided a composite tissue supporting device comprising:

a recoverable member of nickel-titanium shape-memory alloy, said alloy having martensitic and austenitic states and a transition temperature therebetween, said recoverable member being insertable into a patient while in said martensitic state and being elastically deformable while in said martensitic state from a first configuration to a second configuration, said recoverable member providing tissue support while in said second configuration and being recoverable to said first configuration upon heating above said transition temperature to said austenitic state; and a reinforcing member connected to said recoverable member, said reinforcing member supporting said recoverable member when both of said members are deformed from a first configuration to a second configuration, said reinforcing member preventing springback of said recoverable member, the support of said reinforcing member being overcome upon recovery of said recoverable member to its austenitic state for removal of both of said members from a patient.

In yet again another aspect of the invention there is provided a tissue supporting device comprising a recoverable member of nickel-titanium shape-memory alloy, said recoverable member having a first configuration and a second, deformed configuration, said alloy having martensitic and austenitic states and a transition temperature therebetween, said recoverable member being deformable from said first configuration to said second configuration, said recoverable member providing tissue support while in said second configuration and being recoverable to said first configuration upon heating above said transition temperature to said austenitic state.

DESCRIPTION OF THE DRAWING

FIG. 13 discloses yet another embodiment of a stent-like member in the form of a corrugated wire spring which also provides enhanced recovery, as will be discussed later in the specification.

FIG. 10A illustrates a "wish-bone" configuration capable of recovering onto a removal tool (not shown) having a detent complementary with the center portion of the stent-like member. FIG. 10B illustrates a stent-like member having an enlarged center section which can recover onto the bulbous portion of a removal tool (not shown).

FIG. 12 illustrates in exploded perspective view another embodiment of a tissue supporting device in the form of a stent-like member. In FIG. 12A the stent-like member is in its first configuration. In FIG. 12B the member is deformed, for example, into a coil shape outside of the body. In FIG. 12C the deformed stent-like member is inserted within a duct in the body, for example, a tube that has been previously severed and is sewn together around the deformed stent-like member, a portion of the stent-like member extending through the wall of the tube for subsequent retrieval. In FIG. 12D a removal tool has captured the end of the deformed stent-like member and progressively heats portions of the stent-like member, such as by the application of a hot fluid, the stent-like member recovering to its first configuration, as shown in FIG. 12A. FIG. 12E shows the duct and the recovered and removed stent-like member.

FIG. 13 is a perspective view showing another embodiment of a tissue supporting device in the form of a stent-like member in the form of a corrugated wire spring.

DESCRIPTION OF THE PREFERRED EMBODIMENTS

Figure 1:
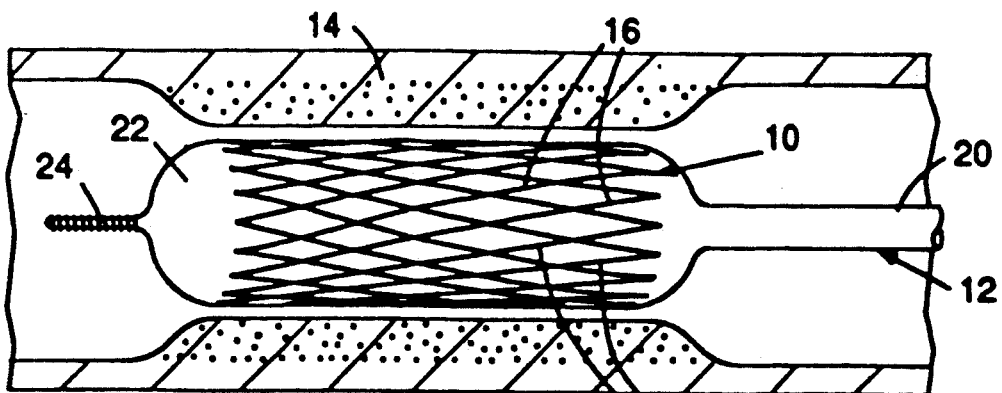
FIG. 1 is a partial cross-sectional view of an embodiment of a tissue supporting device in the form of a stent-like member positioned over a deforming device, shown to be an angioplasty balloon, within a partially occluded artery.

With continued reference to the drawing, FIG. 1 illustrates a tissue supporting device in the form of a stent-like member shown as recoverable member 10 carried by angioplasty device 12 and positioned within a partially or totally occluded artery 14 or other hollow viscus. Recoverable member 10 is radially deformable having a plurality of wire portions 16 and 18 that are at an angle to each other and to the longitudinal axes of tube-like recoverable member 10. It is understood that wire portions 16 and 18 are connected together, as appropriate, to provide the degree of support necessary for recoverable member 10.

Recoverable member 10 is made of shape-memory alloy, preferably nickel-titanium shape-memory alloy, the alloy having a martensitic metallurgical state, an austenitic metallurgical state, and a transition temperature therebetween. Wire portions 16 and 18 may have various cross-sectional shapes, as required.

Shape-memory alloys, i.e., memory metals, are alloys which manifest the shape-memory effect. Such alloys are well known, and they and the shape-memory effect are discussed, for example, in "Shape-Memory Alloys", Scientific American, Vol. 281, pages 74-82 (November, 1979). The shape-memory effect can actually constitute two separate phenomena, one generally referred to as heat-recoverability, and the other phenomenon generally referred to as pseudoelasticity. In reality, the two phenomena are intertwined, and the subject invention takes advantage of each.

Shape-memory alloys are disclosed in U.S. Pat. Nos. 3,012,882 and 3,174,851. As made clear in these patents, these alloys undergo a transition between an austenitic state and a martensitic state at certain temperatures. When they are deformed while in the martensitic state they will retain this deformation as long as they are maintained in this state but will revert to their original configuration when they are heated to a transition temperature, at which time they transform to their austenitic state. The temperatures at which these transitions occur are effected by the nature of the alloy and the conditioning of the material. Nickel-titanium based alloys wherein the transition temperature is slightly higher than body temperature are preferred for the subject invention. It is desirable to have the transition temperature high enough so that the transition temperature will not be reached upon exposure of the body to ambient temperature increases, but low enough such that the alloy can be heated without causing significant damage to the tissues of the body.

The heat-recoverability of recoverable member is illustrated in FIGS. 1-4 wherein recoverable member 10 is deformed while in its martensitic metallurgical state and is subsequently recovered by heating recoverable member 10 through its transition temperature into its austenitic metallurgical state. In FIG. 1, recoverable member 10 is inserted by means of angioplasty device 12 having lumen portion 20, balloon portion 22 and guide portion 24. Recoverable member 10 is positioned about balloon portion 22.

Figure 2:
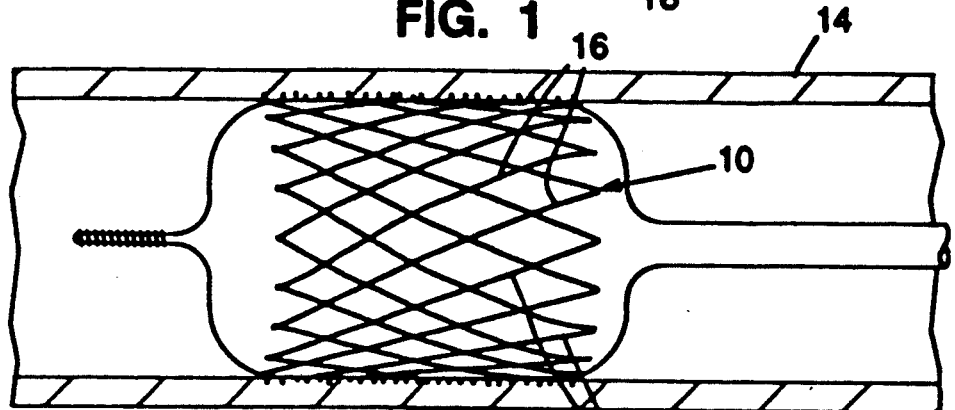
FIG. 2 is a partial cross-sectional view of the stent-like member shown in FIG. 1 after expansion of the angioplasty balloon which has caused elastic deformation of the stent-like member.

In FIG. 2, balloon portion 22 has been expanded, thus deforming recoverable member 10 radially outwardly against occluded artery 14. The cross-section of wire portions 16 and 18 may be optimized to assist in the angioplasty procedure—such as by the use of a wire with a sharp outer edge to pre-incise the tissue thus causing a more uniform dilatation. Although the subject invention is initially being described as a part of an angioplasty procedure, it is understood that the invention is not limited to such a procedure or to the use of a stent-like member in an artery. It should be apparent to one skilled in the art that the subject invention is useful in supporting body issue in general as well as various arteries besides a coronary artery, e.g., in saphenous vein grafts, the vena cavae, the aorta, the renal artery, the iliac artery, the femoral artery, the popliteal artery, the carotid artery, the cranial arteries, pulmonary arteries, etc. The various embodiments of the invention are also useful with other tubular organs including but not limited to the prostate, the biliary tract, the esophagus, the trachea, the fallopian tubes, the vas deferens, the ureters, the tear ducts, the salivary ducts, etc.

Figure 3:
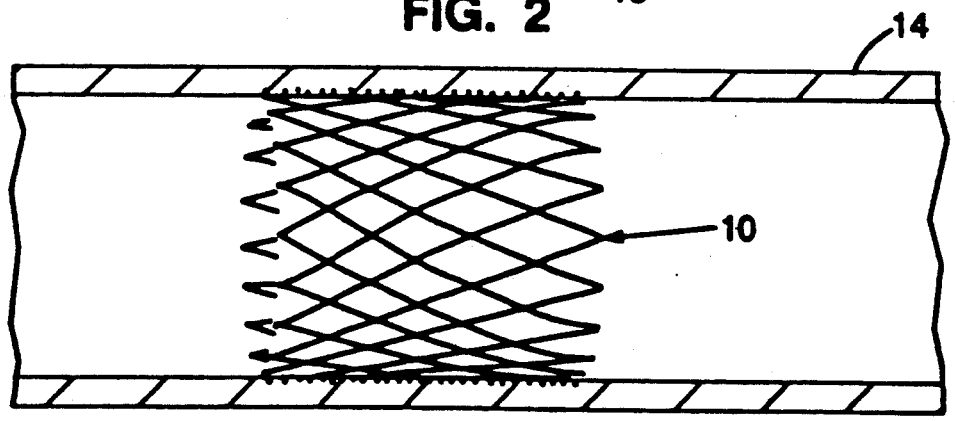
FIG. 3 is a partial cross-sectional view of the stent-like member shown in FIGS. 1 and 2 wherein the angioplasty balloon has been contracted and removed leaving the stent-like member to support the expanded blood vessel.

In FIG. 3, angioplasty device 12 (not shown) has been removed by collapsing the balloon portion, and recoverable member 10 is left in place to support artery 14. After a suitable period of time, as determined by the physician, recoverable member 10 may be removed (unlike the prior art devices discussed earlier). As seen in FIG. 3, the alloy of recoverable member 10 remains in the martensitic metallurgical state to support healing artery 14. Recoverable member 10 has been elastically deformed. The devices disclosed in U.S. Pat. Nos. 4,739,762, 4,776,337 and 4,733,665 exceed the elastic limit of the material of the thin-walled tubular members in the deformation process and consequently destroy material properties. Recoverable member 10 of the subject invention is not permanently deformed and therefore provides improved support to the supple tissue that is being assisted during the healing process.

Figure 4:
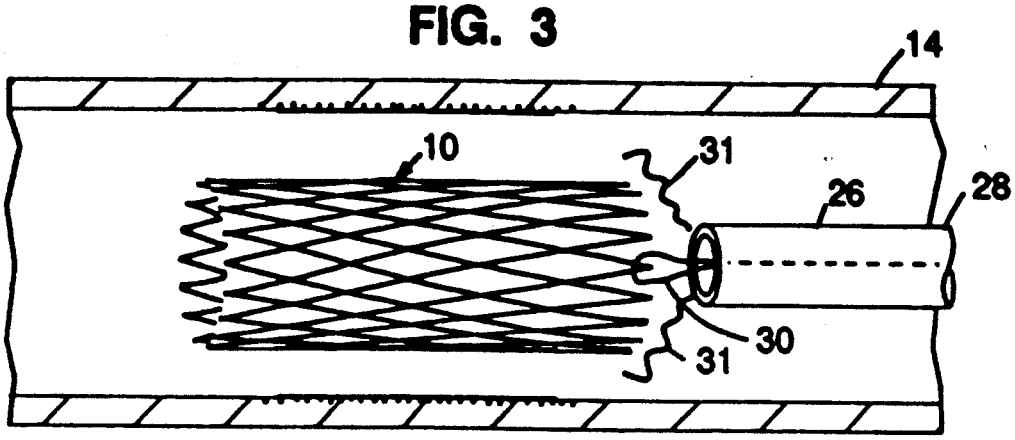
FIG. 4 is a partial cross-sectional view of the stent-like member shown in FIGS. 1–3 wherein said stent-like member has subsequently been heated above its transition temperature and has recovered from its deformed configuration, as shown in FIGS. 2 and 3, to its original configuration, as shown in FIG. 1.

In FIG. 4, removal means 26 is introduced to recover and capture recoverable member 10. For purpose of illustration, removal means 26 is shown to have tube portion 28 and gripping portion 30. Removal means 26 is introduced by a catheter or the like such that gripping portion 30 engages a portion of recoverable member 10. Subsequently, a warm fluid 31 is pumped through tube portion 28 to heat recoverable member 10 above the transition temperature of the alloy to elevate the alloy to its austenitic metallurgical state, thus recovering recoverable member 10 from its second configuration, as shown in FIG. 3, to its first configuration, shown in FIG. 1. Recoverable member 10 is shown in FIG. 4 to have recovered from the deformed second configuration to its first configuration, as shown in FIG. 1. Recoverable member 10 may then be removed.

Another method of obtaining a deformed martensitic state in recoverable member 10 is to cool an appropriately "trained" recoverable member 10 below its martensitic transformation temperature within the body without using an angioplasty device having a balloon portion, as described earlier. Some heat-recoverable alloys after repeated cycling become "trained". This procedure is known to those skilled in the art and can be performed on recoverable member 10 outside of the body. An external mechanical means for expansion is no longer required, and the "trained" recoverable member will spontaneously expand. The trained recoverable member is introduced into the body on a warm catheter device which maintains the member in its recovered austenitic metallurgical state. The member is then allowed to cool and expand. The member can subsequently be retrieved, as described earlier. Such a phenomenon is discussed in *Treatises in Metallurgy* edited by J. F. Tien and J. F. Elliott, 1981, in the chapter entitled "Fundamentals of Martensite Reaction" by M. Cohen and C. M. Wayman. This chapter is incorporated herein by reference. This behavior of the material is often referred to as its "two-way" shape-memory effect.

An alternate embodiment of the subject invention is also illustrated by recoverable member 10, as seen in FIG. 4, wherein recoverable member 10 fabricated from a trained alloy in a first configuration is introduced into the body by a tool similar to removal means 26 and is subjected to warm fluid 31. When recoverable member 10 cools it expands to do work similar to the work performed by the devices disclosed in U.S. Pat. Nos. 4,739,762, 4,776,337 and 4,733,665. However, this is accomplished without the use of an expansion member and, again, with the capability of subsequently being removed completely (unlike the prior art devices) by heating recoverable member 10 through the introduction of a warm fluid to heat the device above the transition temperature of the alloy, as described earlier with regard to FIGS. 1–4.

Figure 5A:
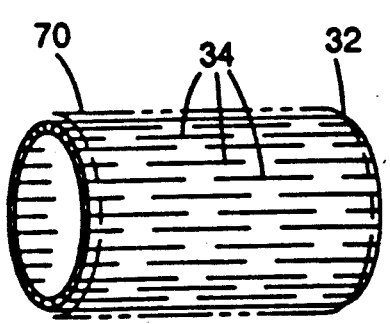
FIG. 5A is a perspective view illustrating an alternate embodiment of a tissue supporting device in the form of a stent-like member having a plurality of longitudinal slots in a first, non-deformed configuration.
Figure 5B:
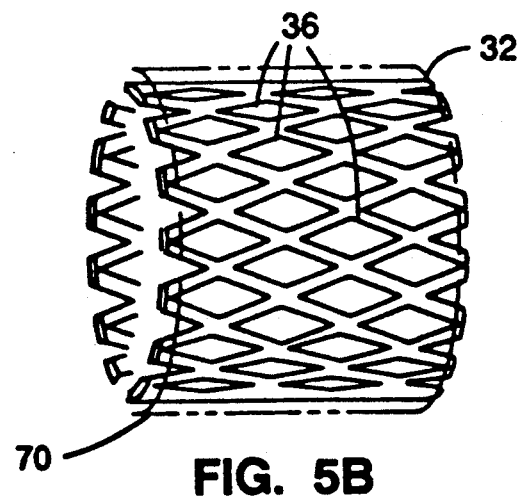
FIG. 5B is a perspective view illustrating the stent-like member of FIG. 5A after deformation (shown in this case to be expansion) creating a lattice-like structure of expanded material.

FIG. 5A illustrates an alternate embodiment of a tissue supporting device in the form of a stent-like member in the form of recoverable member 32 having a plurality of longitudinal slots 34 (which are perforations that are of a particular range) that is generally rectangular and is arranged in a particular pattern that is in the form of a rhombic lattice. FIG. 5B illustrates the expansion of recoverable member 32, which may be referred to as a slotted tube, from its first configuration, shown in FIG. 5A, to its second configuration, shown in FIG. 5B. A rhombic lattice is created by the interconnection of the geometric centers of perforations 36, as clearly seen in FIG. 5B. The rhombic lattice clearly allows expansion or contraction of the grid-like structure. Recoverable member 32, shown in its first configuration in FIG. 5A, is deformed to the second configuration, shown in FIG. 5B, and may be subsequently recovered to the first configuration upon heating recoverable member 32 above the transition temperature of the shape-memory alloy from which it is fabricated. The lattice-like structure disclosed in FIGS. 5A and 5B provides enhanced recovery beyond the 4–9% heat recovery inherent in the shape-memory alloy. U.S. Pat. No. 4,390,599, which is incorporated herein by reference, discloses the enhanced recovery of such a structure. The subject invention is an improvement over that disclosed in the aforementioned patent in that the subject invention applies such a structure to the unique medical application for the clearly advantageous purpose of removing a deformed supporting element using heat recovery of shape-memory alloy.

Figure 6A:
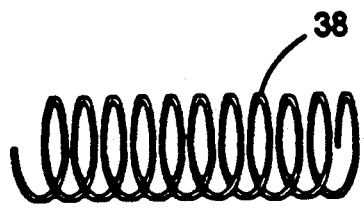
FIG. 6A is a perspective view showing yet another embodiment of a tissue supporting device in the form of a stent-like member in the form of an elongated wire wound spring in a first configuration prior to deformation.
Figure 6B:
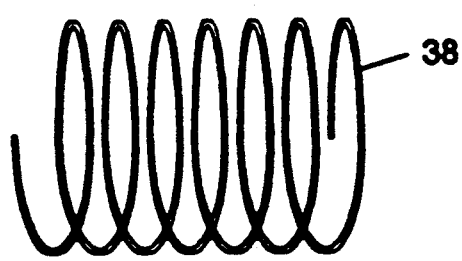
FIG. 6B is a perspective view showing the stent-like member of FIG. 6A after deformation to a second configuration, in this case through radial expansion, the configuration of FIG. 6B being recoverable to the first configuration of FIG. 6A.

FIG. 6A discloses yet another embodiment of a tissue supporting device in the form of a stent-like member in the form of heat-recoverable member 38 which is an elongated wire wound spring-like member including what can be described as a serpentine coil (not shown) which, analogous to the description of the subject invention above, is in a first configuration in FIG. 6A and is in a deformed, second configuration in FIG. 6B.

Figure 7A:
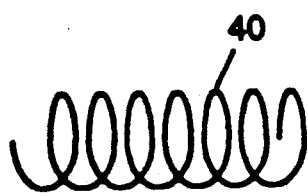
FIG. 7A is a perspective view of yet another embodiment of a tissue supporting device in the form of a recoverable member in a first configuration.
Figure 7B:
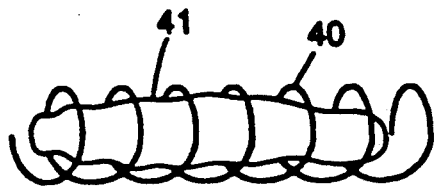
FIG. 7B is a perspective view of the recoverable member of FIG. 7A wherein the member has been deformed longitudinally and placed in the region of a thrombus.
Figure 7C:
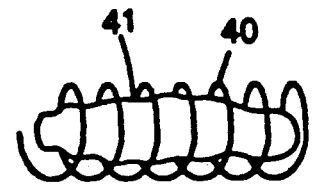
FIG. 7C is a perspective view similar to FIGS. 7A and 7B wherein the member has been recovered axially to the first configuration, shown in FIG. 7A, and in so doing has trapped the thrombus enabling it to be removed when the member is removed.

FIG. 7A is a perspective view of yet another embodiment of a tissue supporting device in the form of a stent-like member in the form of recoverable member 40 which is an elongated helically wound wire-like member of shape-memory alloy which is deformable, as shown in FIG. 7B, longitudinally and which when placed proximate to thrombus 41 and recovered from the second configuration, shown in FIG. 7B, to the first configuration, shown in FIG. 7A, captures thrombus material 41, as seen in FIG. 7C.

Figure 8:
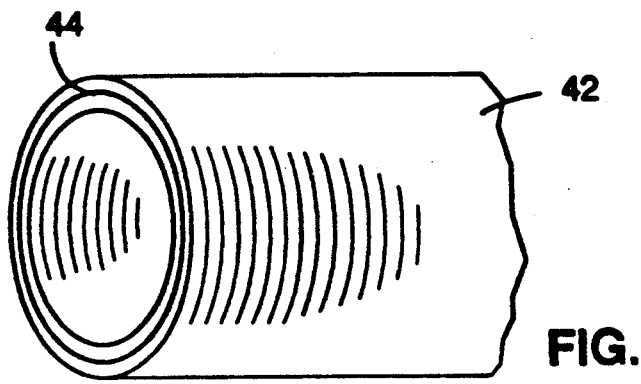
FIG. 8 is a perspective view of a composite tissue supporting device in the form of a stent-like member having a recoverable member (such as any one of those shown in FIGS. 1–6) and a reinforcing member connected and concentrically mounted within the recoverable member, both the recoverable member and the reinforcing member being deformable from the configuration shown in FIG. 8 to another configuration wherein the reinforcing member supplements the strength of the deformed recoverable member to counteract any springback that may be experienced by the deformed recoverable member when the means (not shown) for deforming the recoverable member is removed.

FIG. 8 illustrates yet another embodiment of a tissue supporting device in the form of a stent-like member comprising recoverable member 42 of shape-memory alloy and reinforcing member 44 concentrically mounted within recoverable member 42. Both recoverable member 42 and reinforcing member 44 are deformable from a first configuration to a deformed, second configuration and are recoverable, as discussed above, to the first configuration for removal of the stent-like member. Recoverable member 42 may be similar in structure to any of the recoverable members shown in FIGS. 1–6 and may be deformed by means of expansion within the body by mechanical means to a second configuration and subsequently recovered to its first configuration by elevating the temperature of the device above the transition temperature of the shape-memory alloy. Upon deformation, specifically expansion, of recoverable member 42, some springback to a smaller configuration may be experienced by recoverable member 42 when mechanical deforming means, such as a balloon portion of an angioplasty device (not shown), is removed. Reinforcing member 44 is made from a more ductile material and may be crimped while in the unexpanded state by recoverable member 42 when it is transformed to the austenitic state. It is within the scope of the invention to connect reinforcing member 44 to recoverable member 42 by various means such as laminating, cladding, etc. Suitable materials for reinforcing member 44 are stainless steel, gold, tantalum, etc.

It is understood that it is within the scope of the invention to use various mechanical means to deform the shape-memory alloy recoverable members. FIGS. 1 and 2 illustrate the balloon portion of an angioplasty device being used to expand the deformable member. Other mechanical means such as expandable braided members, a plurality of thin metallic members actuated mechanically to expand in diameter, etc. are considered to be within the scope of the invention.

Figure 9:
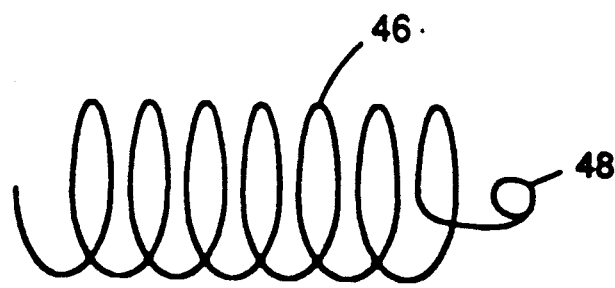
FIG. 9 is a perspective view of a tissue supporting device in the form of a stent-like member which, for purposes of illustration, is shown to be an elongated wire wound spring, similar to that disclosed in FIGS. 6A and 6B, further including a retrieval portion which can be captured by a removal tool after the stent-like member has been inserted, deformed, and subsequently recovered to its original configuration for purposes of removal.

FIG. 9 illustrates recoverable member 46 having retrieval portion 48 shown to be a hook- or eyelet-shaped portion of recoverable member 46. It is within the scope of the invention to provide other apertures or extensions such as a tether wire or the like which may comprise a retrieval portion.

Figure 10A:
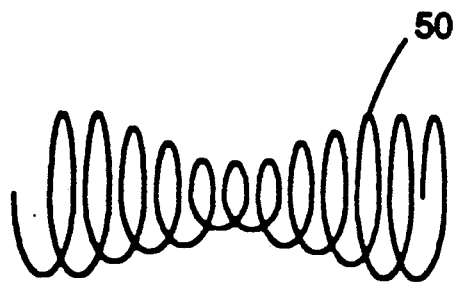
FIGS. 10A and 10B are perspective views similar to FIG. 9 of alternate embodiments of a tissue supporting device in the form of a stent-like member illustrated as elongated wire wound springs wherein the general shape of the stent-like member in its original configuration facilitates the capture and removal of the stent-like member.
Figure 10B:
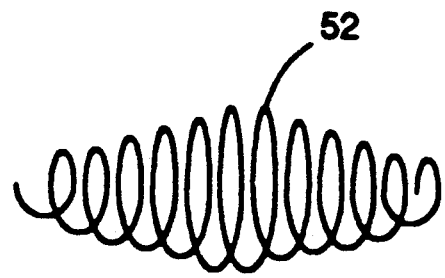

FIGS. 10A and 10B illustrate recoverable members 50 and 52, the overall first configurations of which provide means for retrieval of the members subsequent to heat recovery to their first configurations. Recoverable member 50 is shown to be a wire wound member having a wish-bone configuration which can cinch down on a removal tool having a detent or the like. FIG. 10B illustrates recoverable member 52 having an enlarged center portion which can likewise recover on top of a bulbous portion of a removal tool (not shown) when recovered.

Heat recovery of the various embodiments of recoverable members can be accomplished by a variety of means known to one skilled in the art. FIG. 4 illustrates means to introduce a warm fluid which elevates the temperature above the transition temperature of the alloy. Other means of locally applying heat, such as magnetic inductance, electrical resistance, etc., are considered to be within the scope of the invention.

Figure 11A:
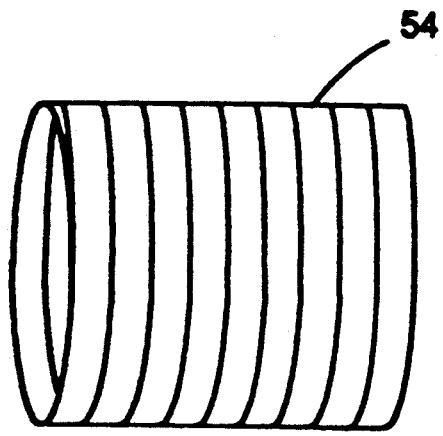
FIGS. 11A and 11B illustrate in perspective view yet another embodiment of a tissue supporting device in the form of a stent-like member wherein the first configuration of the stent-like member is shown in FIG. 11A, and the deformed configuration is shown in FIG. 11B. This embodiment can generally surround and compress the body portion and can be subsequently removed upon expansion from its original configuration.
Figure 11B:
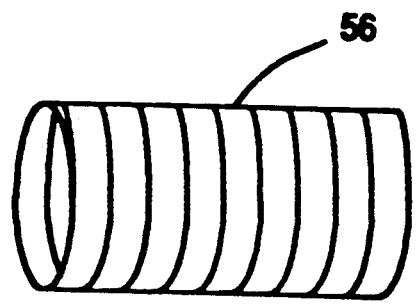

FIGS. 11A and 11B illustrate the concept of recoverable member 54 having a first configuration, as shown in FIG. 11A, which is deformed to a second configuration 56 as shown in FIG. 11B, which is radially smaller to support a component externally rather than internally.

FIG. 12 illustrates yet another embodiment of a tissue supporting device in the form of a stent-like member wherein recoverable member 58 is shown in FIG. 12A to be generally straight in a first configuration and is shown in FIG. 12B to have been deformed outside of the body into a coiled second configuration 60 having a retrieval portion 62. In FIG. 12C coiled second configuration 60 is introduced into the body, such as at the joining of previously severed tubes of the body, e.g., reconnection of the vas deferens previously severed in a vasectomy, and retrieval portion 62 is permitted to extend through the wall of the tube, or vas deferens, 64 during the healing period. In FIG. 12D, recoverable member 58 is shown being removed with the assistance of removal tool 66 shown to be a tube into which retrieval portion 62 has been drawn while warm fluid 67 is pumped through the tube. The result is the progressive recovery of recoverable member 58 from its coiled second configuration 60, shown in FIG. 12B, to its first configuration, as shown in FIG. 12A, while it is being drawn into removal tool 66 through the small opening remaining in the tubular portion of the body. FIG. 12E shows the healed tubular portion of the body with recoverable member 58 fully contained within removal tool 66.

FIG. 13 illustrates yet another stent-like member in the form of recoverable member 68 which is a corrugated wire which has been wound into a coil, the corrugations of the wire allowing enhanced recovery when the wire has been deformed by straightening beyond the point of the overall recovery of the coils which have themselves been deformed by means of expansion.

All of the above-described tissue supporting devices may also be used to deliver drugs or other physical or chemical agents, e.g., electric charge radioactive materials, etc. by either coating any of the recoverable members with drug releasing materials or by providing a separate layer of drug releasing materials. The materials are released by means of contact, dissolution, pressure, etc. See optional coating or layer 70 shown in phantom in FIGS. 5A and 5B. All of the above tissue supporting devices may be coated with biologically inert coatings to improve their biological compatibility, if desired.

While the invention has been particularly shown and described with reference to the preferred embodiments thereof, it will be understood to those skilled in the art that the foregoing and other changes in form and details may be made therein without departing from the spirit and scope of the invention, limited only by a just interpretation of the following claims.

What is claimed is:

1. A tissue supporting device comprising an undeformed, recoverable member of generally tubular shape of nickel-titanium shape-memory alloy, said alloy having martensitic and austenitic metallurgical states and a transition temperature therebetween, the transition temperature being higher than body temperature, said recoverable member being insertable within a patient while in said undeformed, martensitic state and being elastically deformable from a first configuration while in said martensitic state to a second configuration in the martensitic state, said recoverable member providing tissue support while in said second configuration and being recoverable to said first configuration upon heating of said recoverable member above said transition temperature to said austenitic state for removal of said recoverable member from a patient.

2. A device as in claim 1 wherein said recoverable member is deformable radially outwardly to provide support.

3. A device as in claim 2 wherein said recoverable member is an elongated wire wound spring-like member.

4. A device as in claim 3 wherein said wire has a cross-section, said cross-section being non-circular and of assistance in an angioplasty procedure.

5. A device as in claim 2 wherein said recoverable member is a slotted tube.

6. A device as n claim 2 wherein said recoverable member is a cylindrical member having a longitudinal slot in the circumference thereof.

7. A device as in claim 2 wherein said recoverable member is a corrugated wire spring.

8. A device as in claim 1 wherein said recoverable member is deformable axially and radially from said first configuration to said second configuration.

9. A device as in claim 8 wherein said recoverable member is an elongated helically wound wire which is deformable by longitudinal expansion in a patient and recoverable to capture material such as a thrombus between the coils of said member.

10. A device as in claim 1 wherein said shape-memory alloy exhibits "two-way" shape-memory, said device being deployable in the martensitic phase of the alloy and recoverable in the austenitic phase of the alloy.

11. A device as in claim 1 further including delivery means positioned thereon to provide additional material to the patient while in said second configuration.

12. A device as in claim 1 further including coatings positioned on said recoverable member.

13. A composite tissue supporting device comprising:
an undeformed, recoverable member of nickel-titanium shape-memory alloy, said alloy having martensitic and austenitic states an a transition temperature therebetween, the transition temperature being higher than body temperature, said recoverable member being insertable into a patient while in said undeformed, martensitic state and being elastically deformable while in said martensitic state from a first configuration to a second configuration in the martensitic state, said recoverable member providing tissue support while in said second configuration and being recoverable to said first configuration upon heating above said transition temperature to said austenitic state; and
a reinforcing member connected to said recoverable member, said reinforcing member supporting said recoverable member when both of said members are deformed from a first configuration to a second configuration, said reinforcing member preventing springback of said recoverable member, the support of said reinforcing member being overcome upon recovery of said recoverable member to its austentic state for removal of both of said members from a patient.

14. A device as in claim 13 further including delivery means positioned thereon to provide additional material to the patient while in said second configuration.

15. A device as in claim 13 wherein said recoverable member and said reinforcing member are laminated together.

16. A device as in claim 13 wherein said reinforcing member is clad to the inside of said recoverable member.

17. A device as in claim 13 further including coatings positioned on said recoverable member.

18. A tissue supporting device comprising an undeformed, recoverable member of nickel-titanium shape-memory alloy, said recoverable member having a first, undeformed configuration and a second, deformed configuration, said alloy having martensitic and austenitic states and a transition temperature therebetween, the transition temperature being higher than body temperature, said recoverable member being deformable from said first, undeformed configuration to said second, deformed configuration, said recoverable member providing tissue support while in said second, deformed configuration and being recoverable to said first, undeformed configuration upon heating above said transition temperature to said austenitic state.

19. A device as in claim 18 further including delivery means positioned thereon to provide additional material to the patient while in said second configuration.

20. A device as in claim 18 further including coatings positioned on said recoverable member.

* * * * *

UNITED STATES PATENT AND TRADEMARK OFFICE
CERTIFICATE OF CORRECTION

PATENT NO. : 5,197,978
DATED : March 30, 1993
INVENTOR(S) : Robert L. Hess It is certified that error appears in the above-identified patent and that said Letters Patent is hereby corrected as shown below:

Column 5, line 59, after "member", insert --10-- therefor;

Column 10, lin 19, after "as", delete "n", and insert --in-- therefor.

Signed and Sealed this

Fourteenth Day of December, 1993

*Attest:*

BRUCE LEHMAN

*Attesting Officer*     *Commissioner of Patents and Trademarks*

REEXAMINATION CERTIFICATE (2895th)
United States Patent [19]
Hess

[11] B1 5,197,978
[45] Certificate Issued May 28, 1996

[54] REMOVABLE HEAT-RECOVERABLE TISSUE SUPPORTING DEVICE

[75] Inventor: Robert L. Hess, Portola Valley, Calif.

[73] Assignee: Advanced Coronary Technology, Inc., Menlo Park, Calif.

Reexamination Requests:
No. 90/003,416, Apr. 22, 1994
No. 90/003,510, Jul. 27, 1994

Reexamination Certificate for:
Patent No.: 5,197,978
Issued: Mar. 30, 1993
Appl. No.: 691,823
Filed: Apr. 26, 1991

Certificate of Correction issued Dec. 14, 1993.

[51] Int. Cl.$^6$ ............... A61F 2/06; A61M 29/00
[52] U.S. Cl. ............... 623/1; 623/11; 623/12; 606/194
[58] Field of Search ............... 623/1, 11, 12; 606/191–200; 600/36; 604/96; 428/913

[56] References Cited

U.S. PATENT DOCUMENTS

| | | | |
|---|---|---|---|
| 3,585,647 | 6/1971 | Gajewski et al. | 128/334 |
| 3,657,744 | 4/1972 | Ersek | 623/11 |
| 4,030,503 | 6/1977 | Clark | 128/304 |
| 4,046,150 | 9/1977 | Schwartz et al. | 128/328 |
| 4,300,244 | 11/1981 | Bokros | 3/14 |
| 4,326,532 | 4/1982 | Hammar | 128/349 |
| 4,347,846 | 9/1982 | Dormia | 128/328 |
| 4,553,545 | 11/1985 | Maass et al. | 128/341 |
| 4,572,186 | 2/1986 | Gould et al. | 128/341 |
| 4,655,771 | 4/1987 | Wallsten | 623/1 |
| 4,739,762 | 4/1988 | Palmaz | 128/343 |
| 4,856,516 | 8/1989 | Hillstead | 623/1 |
| 4,886,062 | 12/1989 | Wiktor | 128/343 |
| 4,913,141 | 4/1990 | Hillstead | 606/108 |
| 4,921,484 | 5/1990 | Hillstead | 604/104 |
| 4,954,126 | 9/1990 | Wallsten | 600/36 |
| 5,102,417 | 4/1992 | Palmaz | 623/11 |
| 5,201,901 | 4/1993 | Harada et al. | 606/198 |
| 5,242,451 | 9/1993 | Harada et al. | 606/108 |

FOREIGN PATENT DOCUMENTS

| | | |
|---|---|---|
| 62-82975 | 4/1987 | Japan. |
| 62-82976 | 4/1987 | Japan. |
| PCT/JP88/00960 | 9/1988 | Japan. |
| PCT/JP88/01029 | 10/1988 | Japan. |

*Primary Examiner*—Debra S. Brittingham

[57] ABSTRACT

A tissue supporting device, preferably a stent-like member of shape-memory alloy, that is expandable by angioplasty apparatus or the like is subsequently removable by heat recovery to its original, non-expanded configuration.

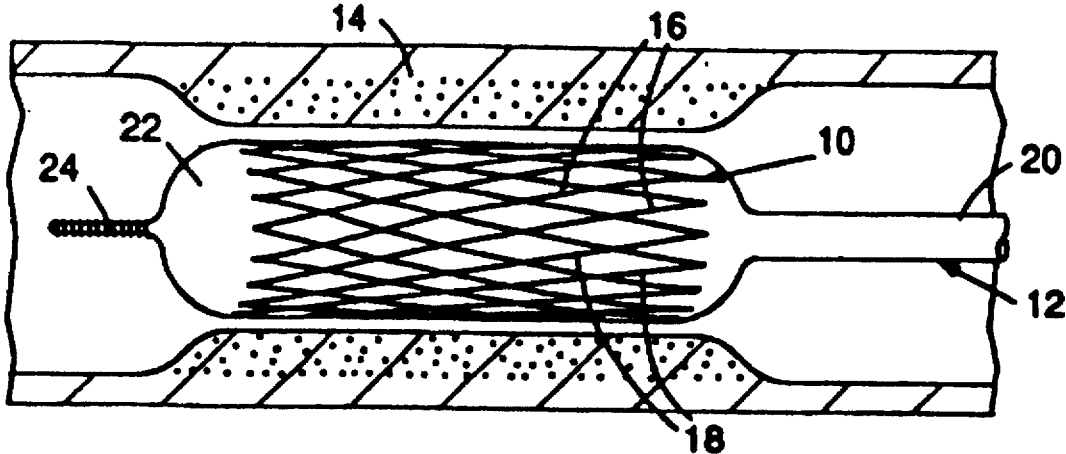

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 18–20 are cancelled.

Claims 1, 13 are determined to be patentable as amended.

Claims 2–12 and 14–17, dependent on an amended claim, are determined to be patentable.

New claim 21 is added and determined to be patentable.

1. A tissue supporting device comprising an undeformed, recoverable member of generally tubular shape of nickel-titanium shape-memory alloy, said alloy having martensitic and austenitic metallurgical states and a transition temperature therebetween, the transition temperature being higher than body temperature, said recoverable member being insertable within a patient while in said undeformed, martensitic state and being elastically deformable from a first configuration while in said martensitic state to a second configuration in the martensitic state, said recoverable member providing tissue support while in said second configuration and being recoverable to said first configuration upon heating of said recoverable member above said transition temperature to said austenitic state for removal of said recoverable member from a patient[.] *and;*

*a reinforcing member within said recoverable member and supporting said recoverable member when both of said members are deformed from the first configuration to the second configuration, the reinforcing member preventing springback of the recoverable member, the support of the reinforcing member being overcome upon recovery of the recoverable member to its austenitic state for removal of both of the members from a patient.*

13. A composite tissue supporting device comprising:

an undeformed, recoverable member of nickel-titanium shape-memory alloy, said alloy having martensitic and austenitic states [an] *and* a transition temperature therebetween, the transition temperature being higher than body temperature, said recoverable member being insertable into a patient while in said undeformed, martensitic state and being elastically deformable while in said martensitic state from a first configuration to a second configuration in the martensitic state, said recoverable member providing tissue support while in said second configuration and being recoverable to said first configuration upon heating above said transition temperature to said austenitic state; and a reinforcing member connected to said recoverable member, said reinforcing member supporting said recoverable member when both of said members are deformed from a first configuration to a second configuration, said reinforcing member preventing springback of said recoverable member, the support of said reinforcing member being overcome upon recovery of said recoverable member to its [austentic] *austenitic* state for removal of both of said members from a patient.

*21. A tissue supporting device comprising an undeformed, recoverable member of generally tubular shape of nickel-titanium shape-memory alloy, said alloy having martensitic and austenitic metallurgical states and a transition temperature therebetween, the transition temperature being higher than body temperature, said recoverable member being insertable within a patient while in said undeformed, martensitic state and being elastically deformable from a first configuration while in said martensitic state to a second configuration in the martensitic state, said recoverable member providing tissue support while in said second configuration and being recoverable to said first configuration upon heating of said recoverable member above said transition temperature to said austenitic state for removal of said recoverable member from a patient, said recoverable member comprising a slotted tube having a plurality of perforations extending parallel to a central axis of the slotted tube with ends of the perforations circumferentially adjacent to each other being offset in an axial direction;*

*a reinforcing member within the recoverable member, the reinforcing member supporting the recoverable member when both of the members are deformed from the first configuration to the second configuration, the reinforcing member preventing springback of the recoverable member, the support of the reinforcing member being overcome upon recovery of the recoverable member to its austenitic state for removal of both of the members from a patient, the reinforcing member being clad to the inside of the recoverable member.*

* * * * *